(12) United States Patent
Roschak et al.

(10) Patent No.: US 12,226,127 B2
(45) Date of Patent: Feb. 18, 2025

(54) REMOTELY ADJUSTABLE INTERACTIVE IMPLANTABLE DEVICE

(71) Applicant: NuVasive Specialized Orthopedics, Inc., San Diego, CA (US)

(72) Inventors: Edmund J. Roschak, Aliso Viejo, CA (US); Thomas B. Buford, Aliso Viejo, CA (US)

(73) Assignee: NuVasive Specialized Orthopedics, Inc., Audubon, PA (US)

( * ) Notice: Subject to any disclaimer, the term of this patent is extended or adjusted under 35 U.S.C. 154(b) by 0 days.

(21) Appl. No.: 17/663,885

(22) Filed: May 18, 2022

(65) Prior Publication Data

US 2022/0273342 A1    Sep. 1, 2022

Related U.S. Application Data

(63) Continuation of application No. 16/398,705, filed on Apr. 30, 2019, now Pat. No. 11,357,547, which is a
(Continued)

(51) Int. Cl.
*A61B 17/68* (2006.01)
*A61B 17/70* (2006.01)
(Continued)

(52) U.S. Cl.
CPC .......... *A61B 17/68* (2013.01); *A61B 17/7016* (2013.01); *A61B 17/7216* (2013.01);
(Continued)

(58) Field of Classification Search
CPC .......................... A61B 2017/681; A61B 17/68
See application file for complete search history.

(56) References Cited

U.S. PATENT DOCUMENTS

| 2,702,031 A | 2/1955 | Wenger |
| 3,111,945 A | 11/1963 | Solbrig |

(Continued)

FOREIGN PATENT DOCUMENTS

| CN | 1697630 A | 11/2005 |
| CN | 101040807 A | 9/2007 |

(Continued)

OTHER PUBLICATIONS

Abe et al., "Experimental external fixation combined with percutaneous discectomy in the management of scoliosis.", SPINE, 1999, pp. 646-653, 24, No. 7.
(Continued)

*Primary Examiner* — Tessa M Matthews

(57) ABSTRACT

Systems and methods for adjusting a curvature of a spine are provided. The systems may include an implant body, an actuator coupled to the implant body, a sensor configured to detect a parameter indicative of a biological condition, a transceiver, and a controller. The transceiver may be configured to transmit data associated with the parameter to an external remote control and receive instructions from the external remote control. Finally, the controller is configured to move the actuator in response to the instructions from the external remote control, wherein the actuator adjusts the implant body. The methods may include measuring a parameter indicative of a biological condition; transmitting data associated with the parameter from the implantable device to an external remote control; transmitting instructions from the external remote control to the implantable device; and actuating the implantable device in response to the instructions from the external remote control.

19 Claims, 11 Drawing Sheets

Related U.S. Application Data continuation of application No. 15/521,025, filed as application No. PCT/US2015/057010 on Oct. 22, 2015, now Pat. No. 10,314,619.

(60) Provisional application No. 62/067,937, filed on Oct. 23, 2014.

(51) Int. Cl.

| | | |
|---|---|---|
| A61B 17/72 | (2006.01) | |
| A61B 5/00 | (2006.01) | |
| A61B 5/01 | (2006.01) | |
| A61B 5/0205 | (2006.01) | |
| A61B 5/026 | (2006.01) | |
| A61B 5/053 | (2021.01) | |
| A61B 5/107 | (2006.01) | |
| A61B 5/145 | (2006.01) | |
| A61B 17/00 | (2006.01) | |

(52) U.S. Cl.
CPC ............ *A61B 5/01* (2013.01); *A61B 5/02055* (2013.01); *A61B 5/026* (2013.01); *A61B 5/053* (2013.01); *A61B 5/1072* (2013.01); *A61B 5/14539* (2013.01); *A61B 5/4504* (2013.01); *A61B 5/4509* (2013.01); *A61B 5/4836* (2013.01); *A61B 5/686* (2013.01); *A61B 2017/00022* (2013.01); *A61B 2017/00402* (2013.01); *A61B 2017/00407* (2013.01); *A61B 2017/00867* (2013.01); *A61B 2017/681* (2013.01); *A61B 2560/0475* (2013.01); *A61B 2562/0261* (2013.01)

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |

(56) References Cited

U.S. PATENT DOCUMENTS

| | | |
|---|---|---|
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,559,951 B2 | 7/2009 | DiSilvestro ............ A61F 2/36 623/23.47 |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |

(56) References Cited

U.S. PATENT DOCUMENTS

| | | |
|---|---|---|
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan ............... A61B 5/4504 606/62 |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 9,445,720 B2 | 9/2016 | Janna .................... A61B 5/4504 |
| 9,883,896 B2 | 2/2018 | Kim et al. |
| 10,314,619 B2 | 6/2019 | Roschak ............ A61B 17/7016 |
| 10,702,375 B2 | 7/2020 | Roholt ................... A61F 2/1635 |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | Mcclendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1* | 3/2006 | DiSilvestro ............... A61F 2/38 623/23.45 |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |

(56) References Cited

U.S. PATENT DOCUMENTS

| | | |
|---|---|---|
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2009/0306717 A1* | 12/2009 | Kercher ............. A61B 17/7011 606/279 |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1* | 8/2011 | Forsell ............... A61B 17/7062 606/86 R |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2011/0319755 A1 | 12/2011 | Stein .................... A61F 2/4657 600/437 |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0025587 A1 | 1/2015 | Kim et al. |
| 2015/0105782 A1 | 4/2015 | D'Lima et al. |
| 2015/0105824 A1 | 4/2015 | Moskowitz et al. |
| 2016/0367297 A1* | 12/2016 | Nill .................... A61B 17/7216 |
| 2018/0110543 A1* | 4/2018 | Ingalhalikar ....... A61B 17/7025 |
| 2018/0338782 A1* | 11/2018 | Castelein ........... A61B 17/705 |
| 2019/0269438 A1* | 9/2019 | Simpson ............ A61B 17/7017 |
| 2019/0298417 A1* | 10/2019 | Barrett ............... A61B 17/7041 |

FOREIGN PATENT DOCUMENTS

| | | |
|---|---|---|
| DE | 1541262 A | 6/1969 |
| DE | 8515687 U | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 7/2012 |
| JP | H0956736 | 3/1997 |
| JP | 2002500063 A | 1/2002 |
| WO | WO1998044858 A1 | 1/2002 |
| WO | WO1999051160 A1 | 1/2002 |
| WO | WO2001024697 A1 | 1/2002 |
| WO | WO2001045485 A3 | 1/2002 |
| WO | WO2001045487 A2 | 1/2002 |
| WO | WO2001067973 A2 | 1/2002 |
| WO | WO2001078614 A1 | 1/2002 |
| WO | WO2007015239 A3 | 1/2008 |
| WO | WO2007013059 A3 | 4/2009 |
| WO | WO2011116158 A3 | 1/2012 |
| WO | WO2013119528 A1 | 8/2013 |
| WO | WO2014040013 A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

(56) References Cited

OTHER PUBLICATIONS

Angrisani et al., "Lap-Band® Rapid Port™ System: Preliminary results in 21 patients", Obesity Surgery, 2005, p. 936, 15, No. 7.
Baumgart et al., "A fully implantable, programmable distraction nail (Fitbone)—new perspectives for corrective and reconstructive limb surgery.", Practice of Intramedullary Locked Nails, 2006, pp. 189-198.
Baumgart et al., "The bioexpandable prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", SPINE, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harbach et al., "First experiences with the routine use of the Rapid Port™ system with the Lap-Band®.", Obesity Surgery, 2006, p. 418, 16, No. 4.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.

(56) References Cited

OTHER PUBLICATIONS

Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work ?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", SPINE, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 23 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", SPINE, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.

(56) References Cited

OTHER PUBLICATIONS

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.
International Search Report and Written Opinion for application serial No. PCT/US2015/057010 dated Jan. 8, 2016.

\* cited by examiner

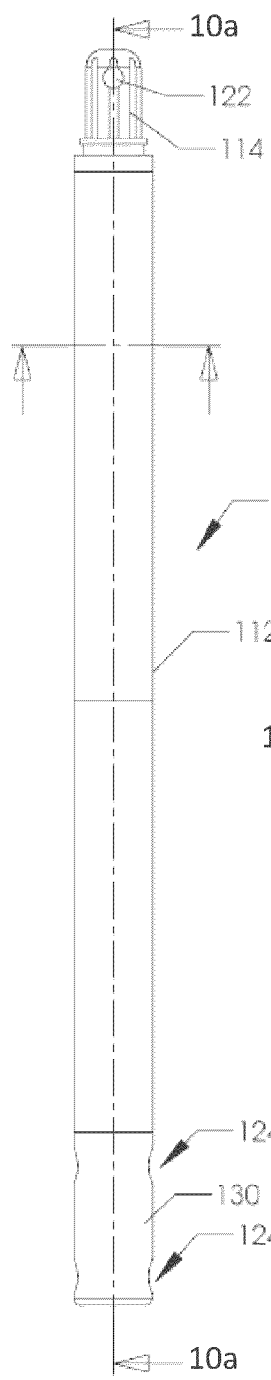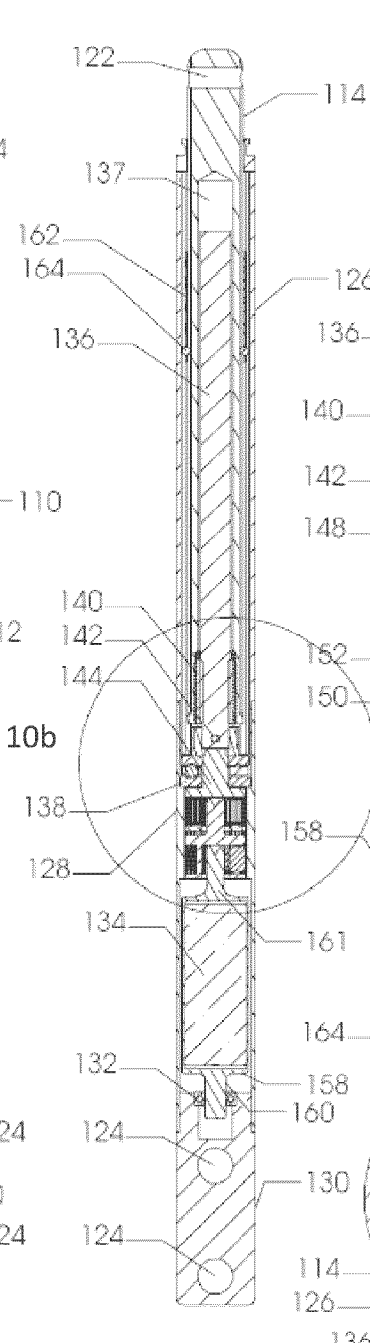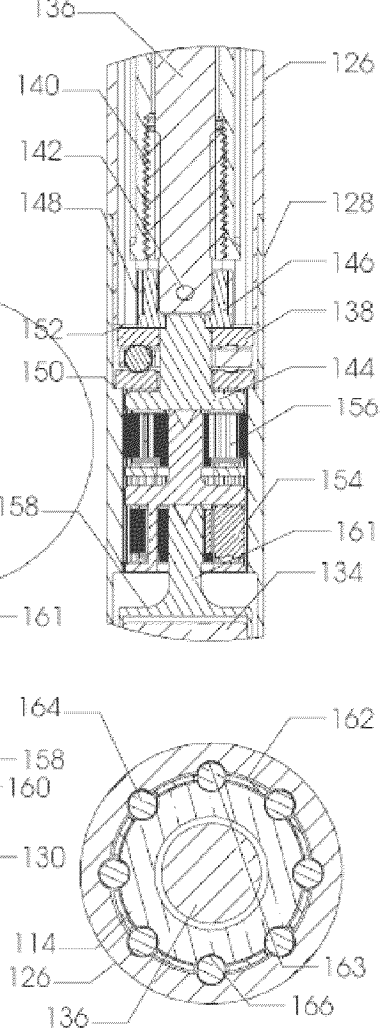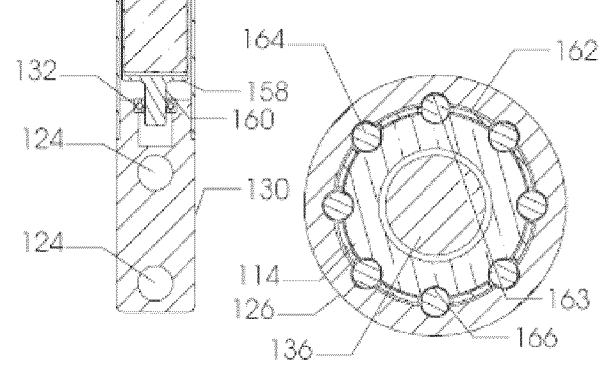

REMOTELY ADJUSTABLE INTERACTIVE IMPLANTABLE DEVICE

CROSS REFERENCE TO RELATED APPLICATIONS

The present patent application is a continuation of U.S. patent application Ser. No. 16/398,705, filed Apr. 30, 2019, which is a continuation of U.S. patent application Ser. No. 15/521,025, filed Apr. 21, 2017, which is a US national stage entry under 35 USC 371 of International Patent Application No. PCT/US15/57010, filed Oct. 22, 2015, which claims priority to U.S. Provisional Patent Application No. 62/067,937, filed Oct. 23, 2014. Each of the foregoing is incorporated by reference as though fully set forth herein.

BACKGROUND

The present invention relates to orthopedic methods and devices for the gradual modification of bones or correction of bone deformities. In particular, the present invention relates to a variety of bone reshaping devices configured to perform procedures, including the lengthening of a bone, the shortening of a bone, the healing of a fracture, the changing of a bone angle, the rotation of a bone, the adjustment of the curvature or torsion of a bone, the realignment or repositioning of a joint or a vertebra, the reforming or supporting of the shape of the spinal column, or combinations thereof, all of which are considered species of "reshaping" as used herein. More specifically, the present invention relates to methods and systems concerning bone reshaping devices that can be externally adjusted based on measured parameters indicative of biological conditions.

External fixation devices, adjustable in length and angular attitude, are commonly utilized for correcting certain angular and longitudinal defects of long bones of limbs. Such fixation devices essentially comprise clamps which hold groups of bone screws inserted in the portions of the bone affected by defects, such clamps being slidably mounted on elements or guides longitudinally positionable externally to the limb to be treated.

The correction is normally carried out gradually with the aid of compression/distraction devices which act on the mobile clamps while the bone callous regenerates itself permitting its manipulation until the desired correction is obtained.

For example, in limb lengthening, the bone is commonly surgically divided into two segments, and wires and half pins are inserted into bone segments above and below the surgical bone cut and are attached to rings of a rigid framework interconnected by struts or telescopic connection rods. The rigid framework is used to gradually push the two bone segments apart longitudinally over a period of time (e.g., one millimeter a day). This allows the bone to gradually form in the gap between bone segments created by this distraction technique. Once the desired amount of lengthening is achieved (e.g., 5-6 cm), the external apparatus is stabilized into a fixed position and left on the bone segments until complete mineralization of the newly formed bone occurs (e.g., 3-6 months, depending on the nature of pathology and amount of lengthening).

Similarly, in deformity correction, the bone is surgically divided (usually at the apex of the deformity) into two segments, and wires and half pins are inserted into bone segments above and below the surgical bone cut and attached to rings of a rigid framework. Opposite rings of the rigid framework are connected together by threaded rods with attached uni-planar or multi-planar hinges and angular distractors that are used to gradually push the two bone segments apart angularly over a period of time.

The use of such external fixation devices can present certain disadvantages. The external fixator can be unwieldy, painful for the patient, and also subjects the patient to the risk of pin track infections, joint stiffness, loss of appetite, depression, cartilage damage, and other side effects. Having the external fixator in place also delays the beginning of rehabilitation. In some circumstances, the visibility of the external fixator can lead to patient embarrassment or insecurity.

In response to these shortcomings, the art developed implantable devices that could be positioned under the skin and/or in bones. These devices were designed to correct bone deformities by applying force to bones, including compressive forces to promote healing, distractive forces to promote lengthening, and angular forces to change the angle/curvature of bones. Some desirable aspects of these implantable devices were that they could apply steady forces over defined periods of time, did not have external wires or rods that could bother the patient or cause pain, had reduced risks of infections, and were not readily visible.

Yet, even these implantable devices could have limitations as well in some cases. For example, because of their location under the skin, some implants could be difficult for care providers to observe, monitor, and adjust. As such, additional surgical procedures would sometimes be performed to incrementally adjust an implant as therapeutically required. The additional surgical procedures exposed patients to increased risks of infection, longer healing times, injury, and increased pain.

In other cases, even where adjustments to implants could be made through the skin, the therapeutic effects of the implant could be less than optimal. Under-application of force could lead to poor bone reformation and/or require longer recovery times. Over-application of force could lead to injury, further bone deformation, and also longer recovery times. Moreover, frequent visits to see a practitioner for adjustments could be time consuming or otherwise inconvenient for a patient.

Thus, notwithstanding the efforts of the prior art, there remains a need for an improved technology for controlling implantable bone reshaping devices in order to improve their performance and efficacy.

SUMMARY

In accordance with one embodiment, a bone growth device is provided. The bone growth device comprises an implant body, an actuator, a sensor, a transceiver, and a controller. The actuator is coupled to the implant body. The sensor is configured to detect a measurable parameter indicative of a biological condition. The transceiver is configured to transmit data associated with the measurable parameter to an external remote control and receive instructions from the external remote control. Finally, the controller is configured to move the actuator in response to the instructions from the external remote control, wherein the actuator adjusts the implant body.

In accordance with another embodiment, an external remote control for a bone growth device is provided. The external remote control comprises a first transceiver, an input, and a controller. The first transceiver is configured to receive data associated with a measurable parameter from the bone growth device and to transmit instructions for the bone growth device. The input is for receiving care information from a care provider. Finally, the controller is configured to: (1) receive the data associated with a measurable parameter and care information and (2) generate the instructions for the bone growth device based on at least one of the data associated with a measurable parameter and care information.

In accordance with another embodiment, a method for treating a patient using an implantable device is provided. The method comprises the steps of: measuring a measurable parameter indicative of a biological condition; transmitting data associated with the measurable parameter from the implantable device to an external remote control; transmitting instructions from the external remote control to the implantable device; and actuating the bone growth device in response to the instructions from the external remote control.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 9 is a side view of a bone reshaping device, adapted for axial lengthening and shortening.

FIG. 10a illustrates a longitudinal cross-section view of the device of FIG. 9, taken along lines 10a-10a.

FIG. 10b illustrates a detailed view of the lengthening device of FIG. 10a, from the area of circle 10b.

DETAILED DESCRIPTION

Various embodiments are described herein, which provide methods and systems related to bone reshaping devices that can be externally controlled and adjusted in response to parameters measured by the implant, to enable therapy to be optimized for each patient in response to measurable indicium of biological response obtained from the sensors on the implant.

It will be of course understood that various omissions, substitutions, and changes in the form and details of the alternatives illustrated can be made without departing from the spirit of the disclosure. Additionally, the various features and processes described herein can be used independently of one another, or can be combined in various ways. All possible combinations and sub-combinations are intended to fall within the scope of this disclosure. Many of the alternatives described herein include similar components, and as such, these similar components can be interchanged in different aspects of the invention.

There has been a long felt need for implantable bone shaping devices that can be effectively and/or adaptively adjusted for therapy. The present disclosure describes a number of illustrative examples detailing how an implant may measure parameters of a patient indicative of a biological condition (e.g., osteogenesis), and interpret or display such information for further therapeutic treatment.

Examples of conditions contemplated as potentially treatable in accordance with the present invention include congenital deformities (birth defects), such as congenital short femur; fibular hemimelia (absence of the fibula, which is one of the two bones between the knee and the ankle); hemiatrophy (atrophy of half of the body); and Ollier's disease (also known as multiple endochondromatosis, dyschondroplasia, and endochondromatosis); developmental deformities, such as neurofibromatosis (a rare condition which causes overgrowth in one leg); and bow legs, resulting from rickets (rachitis) or secondary arthritis; post-traumatic injuries, such as growth plates fractures; malunion or non-union (when bones do not completely join, or join in a faulty position after a fracture); shortening and deformity; bone defects; infections and diseases, such as osteomyelitis (a bone infection, usually caused by bacteria); septic arthritis (infections or bacterial arthritis); and poliomyelitis (a viral disease which may result in the atrophy of muscles, causing permanent deformity); reconstruction after removal of tumors; short stature, such as achondroplasia (a form of dwarfism where arms and legs are very short, but torso is more normal in size); constitutional short stature; and others as may be apparent to those of skill in the art in view of the disclosure herein.

Figure 1:
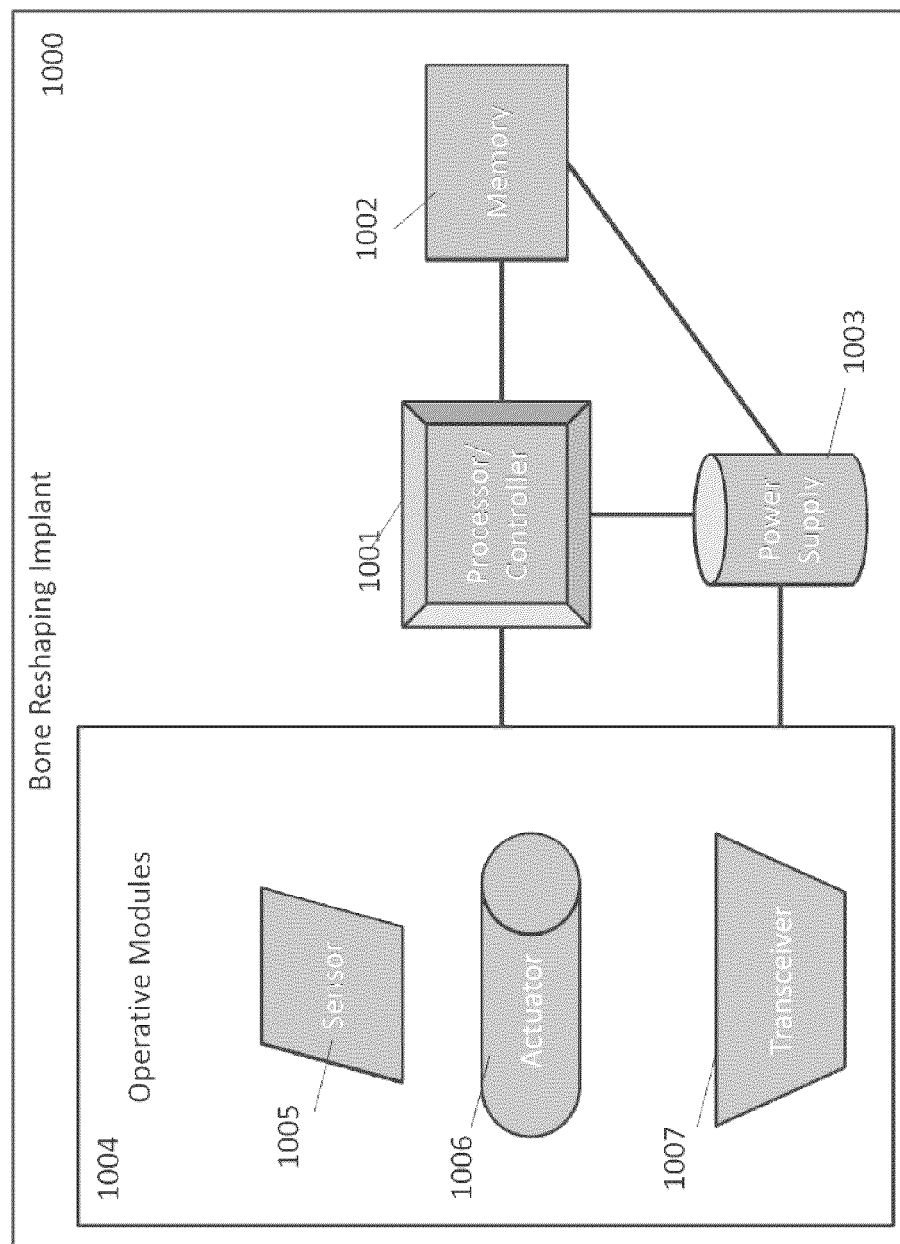
FIG. 1 is a high level schematic of an example bone reshaping implant.

FIG. 1 shows an example high level schematic of a bone shaping implant 1000. Bone shaping implant 1000 has a number of operative modules 1004. These operative modules may include a sensor 1005, actuator 1006, and transceiver 1007. In some embodiments, the sensor 1005 may be onboard to the implant as illustrated in this example. However, the sensor may also be off-board or adjacent to the processor, which will be later illustrated and described. The sensor 1005 may include: a foil strain gauge; a semiconductor strain gauge; a stress sensor; a pH sensor; a thermometer; a pressure sensor; a displacement sensor (e.g., a film resistor where resistance changes as film is stretched); an electrical conductivity/resistance sensor; an acoustic conductivity/resistance sensor; a bio sensor (e.g., a sensor configured to sense the presence or aggregation of platelets, erythrocytes, growth factors, and other biological facilitators of bone healing); and/or any other sensor known in the art for measuring biologically or physiologically relevant data.

These aforementioned sensors may be used to measure parameters that are indicative of a biological condition, such as osteogenesis, ossification, osteoconduction, osteoinduction, and osteopromotion. In some cases, the measured parameters may indicate a deficiency, such as aplastic anemia, additional bone fractures, brittle bones, or improper bone healing. The measured parameters may also allow the calculation of blood flow, bone mass, bone composition, bone density, bone thickness, bone perfusion, bone strength, and bone oxygenation. The sensors may also be generally configured to measure other biological parameters, such as temperature, pulse, blood flow, blood oxygenation, body composition, respiration, cardiac activity, movement, blood volume, pH, heart-beat, metabolism, and blood composition.

Actuator 1006 may be actuated by a driven magnet system, electrical motor, solenoid/ratchet system, piezoelectric system (e.g., an inchworm motor), shape memory alloy (e.g., Nitol), magnetostrictive elements, gesticulation, and/or any way of driving an actuator known in the art. The movement of the actuator 1006 may drive a modification of the bone shaping implant such as: axial elongation; axial shortening; bending (e.g., deformity correction); twisting (e.g., trauma); expression of active media (e.g., releasing treatment or growth factors); delivery of therapeutic current, ultrasound, radio waves, or magnetic flux across a fracture or bone; delivery of therapeutic compression or vibration across a fracture or bone (e.g., a 1 Hz vibration); any therapeutic delivery of movement, energy, or substances; and/or, any combination of the aforementioned provisions. The active media might include HMG-CoA reductase, epidermal growth factor (EGF), vascular endothelial growth factor (VEGF), fibroblast growth factor (FGF), anti-microbials, and/or antibacterials. More active media that promote bone growth are described in U.S. Patent Pub. 2012/0276205, which is incorporated herein by reference. These active media may be delivered by the actuator 1006, or otherwise administered to a patient to facilitate bone adjustment.

Transceiver 1007 may be configured to communicate with other internal and external components. For example, transceiver 1007 may be configured to send and receive information to an internal sensor, such as sensor 1005. Also, for example, transceiver 1007 may transmit/receive data to an external source, such as an external remote control (ERC) device. In some embodiments, transceiver 1007 may transmit data obtained by sensor 1005, processor/control 1001, memory 1002, or any part of the bone reshaping implant 1000 to an external source, such as an ERC. This data may be raw data (e.g., changes in electrical current), measured parameters (e.g., temperature, displacement, or strain), processed information (e.g., a status or biological condition), instructions, interrogatory signals, or any other data, information, or signal relevant to the implant or external device. In some cases, the transceiver 1007 may transmit post action status information to an external device, such as an ERC. For example, such information may include treatment histories, status logs, diagnostic information, recorded data from sensor 1005, and/or data concerning a biological condition.

Transceiver 1007 may also be configured to communicate using Bluetooth (e.g., Bluetooth low energy), ZigBee, Wi-Fi, induction wireless data transmission, medical implant communication service (MICS), radio frequencies, near-field communication (NFC), global system for mobile communications (GSM), or any other form of wireless data transmission.

In certain embodiments, transceiver 1007 may be further configured to communicate directly or indirectly with another external device, such as a data cloud, personal computer, cellular phone, pager, tablet, mobile device, hospital system, or any other device used by a patient or care provider. In some circumstances, it may be desirable for the implant to transmit diagnostic, status, and/or treatment information to a care provider so that the care provider can evaluate the performance of an implantable device, such as implant 1000, and provide recommendations or actually execute therapy to the patient. In some cases, the external device may transmit back to the implant status information, firmware updates, treatment instructions, recommendations, security locks, or other data, information, or protocols relevant to the performance of the implant and/or treatment of the patient.

The operative modules 1004 may be coupled to a processor/controller 1001 to perform operations such as transmitting/receiving data through transceiver 1007, processing sensor data from sensor 1005, controlling actuator 1006, managing system functions, etc. The processor/controller 1001 may also be coupled to memory 1002, which may include volatile and non-volatile memory, and may provide instructions and data to processor/controller 1001. Processor/controller 1001 typically performs logical and arithmetic operations based on program instructions stored within the memory 1002. The instructions in the memory 1002 may be executable to implement the methods described herein. Processor/controller 1001 may also contain or be coupled to a clock for timing therapies.

A power supply 1003 may be coupled to the processor/controller 1001, memory 1002, and/or operative modules 1004 in order to provide operative energy. The power supply 1003 may be a battery, such as a lithium battery, lithium ion battery, nickel-cadmium battery, nickel-metal hydride battery, nickel-hydrogen battery, carbon-zinc battery, silver-oxide battery, zinc-carbon battery, zinc-air battery, mercury oxide battery, alkaline battery, or any other type of battery known in the art and suitable for subcutaneous implantation. Certain batteries may be rechargeable by an external stimulus, or a transient transcutaneous connection. The power supply may also comprise fuel cells, capacitors, inductive coupling, motion powered piezoelectric, motion powered electromagnetic generators, transcutaneous ports (such as ports for hydraulic connections, electrical connections, and other connections to convey power) and/or energy scavenging systems (e.g., systems that use body heat, respiration cycles, body movement, or biochemical reactions). The power supply 1003 may be selected based on factors such as life (e.g., battery life), biocompatibility, power, rechargability, size, current and voltage output, cost, replaceability, the presence or absence of movable parts, and other factors related to performance in an implantable device.

The power supply may also be managed by a power management strategy depending on the power demands. For example, the power management strategy might institute powered, sleep, and idle cycles. In some cases, the power management strategy might take into account the total power and total intended useful life of implant 1000. In some cases, the power management strategy is implemented by the processor/controller 1001.

Figure 2:
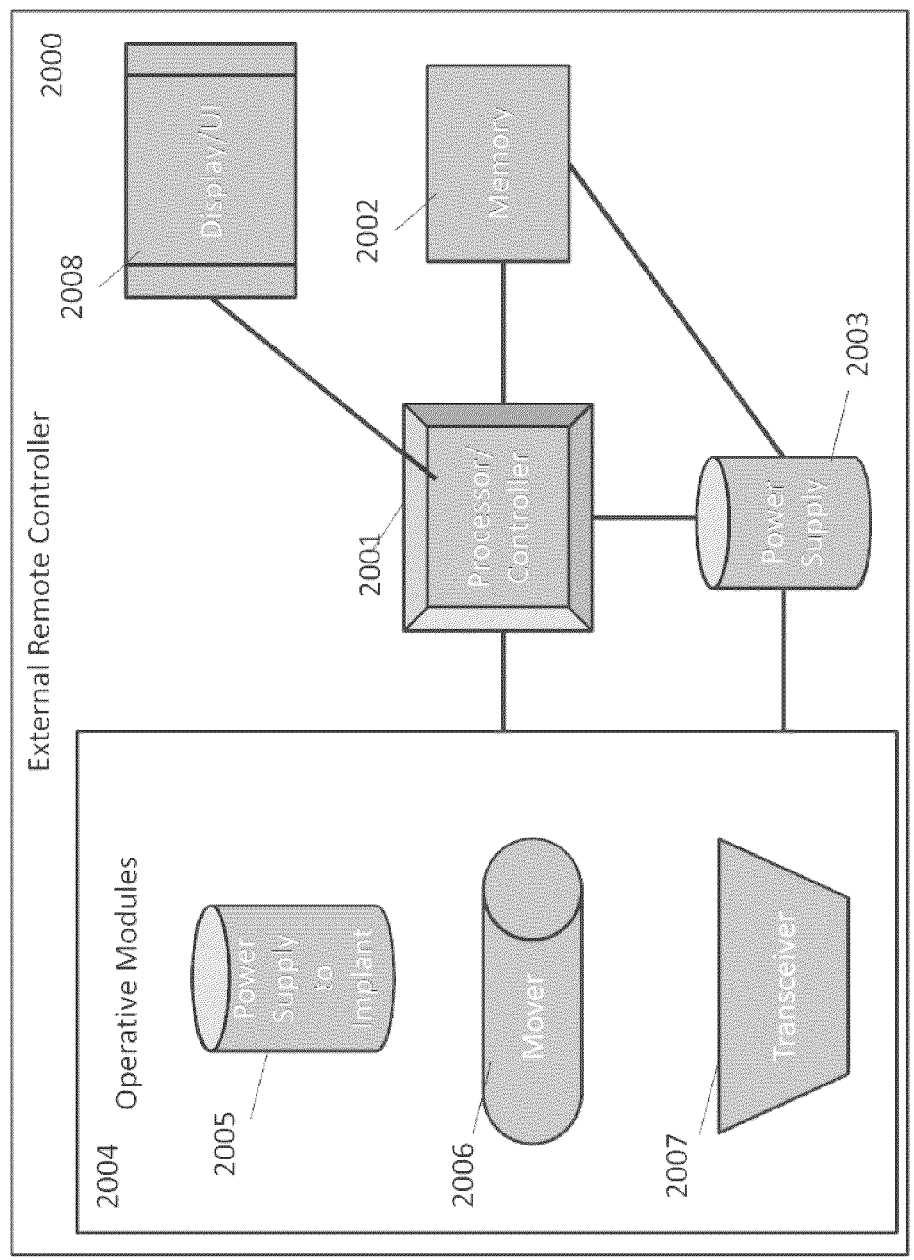
FIG. 2 is a high level schematic of an example external remote controller.

FIG. 2 shows an example high level schematic of ERC 2000. ERC 2000 has a number of operative modules. An optional power supply to implant 2005 may be used to supply power to any part of the implant 1000 including the power supply 1003, the processor 1001, the memory 1002, or any of the operative modules 1004. Power supply to implant 2005 may supply energy through a transcutaneous port, such as transcutaneous ports for electric or hydraulic connections, or any sort of transcutaneous connection (e.g., needle penetration to deliver power or fuel). Power supply to implant 2005 may also supply power by facilitating an energy scavenging system. For example, the bone reshaping implant 1000 may receive power by obtaining energy from body heat, the respiration cycle, body movement, biochemical reactions, and/or any form of energy that may already be available in the human body. Power supply to implant 2005 may escalate those operations to supply more power to the implant 1000. By way of illustration, if implant 1000 received energy from body heat, power to implant may contain a chemical and/or heating apparatus administered to raise the temperature at the location of the implant.

The power supply to implant 2005 may also produce motion, vibrations, electric current, magnetisms, inductance, or capacitance in order to provide power to the implant 1000, which may contain, for example, a motion powered electromagnetic generator, a motion powered piezoelectric motor, coupled inductors, capacitors, batteries, and/or any power supply described in this disclosure or known in the art.

Mover 2006 may cause (e.g., stimulate) bone reshaping implant 1000 to move. For example, mover 2006 may cause actuator 1006 to move by supplying mechanical, electrical, magnetic, capacitive, inductive, or any other type of force or energy to the actuator. Certain illustrative examples of such movement will be discussed further in this disclosure. For example, mover 2006 may include magnets that rotate driven magnets within a telescopic implant. The rotation of mover 2006 causes the implant to lengthen and/or shorten.

Transceiver 2007 is configured to communicate with other internal or external components. For example, transceiver 2007 may transmit or receive information from an implantable device, such as implant 1000. In some embodiments, transceiver 2007 may communicate with an implant's transceiver, such as transceiver 1007, to exchange information including raw data (e.g., changes in electrical current), measured parameters (e.g., temperature, displacement, or strain), processed information (e.g., a status, or biological condition), instructions, interrogatory signals, or any other data, information, or signal relevant to the implant or external device.

In certain embodiments, transceiver 2007 may be further configured to communicate with another external device, such as a data cloud, personal computer, cellular phone, pager, tablet, mobile device, hospital system, or any other device used by a patient or care provider. In some circumstances, it may be desirable for the ERC to transmit diagnostic, status, and/or treatment information to a care provider so that the care provider can evaluate the performance of an implantable device, such as implant 1000, and provide services to the patient. In some cases, the external device may transmit back to the ERC status information, firmware updates, treatment instructions, recommendations, security locks, or other data relevant to the performance of the implant and/or treatment of the patient.

Transceiver 2007 may be configured to communicate using Bluetooth (e.g., Bluetooth low energy), ZigBee, Wi-Fi, induction wireless data transmission, medical implant communication service (MICS), radio frequencies, near-field communication (NFC), global system for mobile communications (GSM), or any other form of wireless data transmission.

The operative modules 2004 may be coupled to a processor/controller 2001 to perform operations such as transmitting/receiving data through transceiver 2007, controlling power supply to implant 2005, controlling mover 2006, managing system functions, etc. The processor/controller 200 I may also be coupled to memory 2002, which may include volatile and/or non-volatile memory, and may provide instructions and data to processor/controller 2001. Processor/controller 2001 typically performs logical and arithmetic operations based on program instructions stored within the memory 2002. The instructions in the memory 2002 may be executable to implement the methods described herein. The processor/controller 2001 may also contain or be coupled to a clock for timing therapies. In some circumstances, the processor/controller 2001 may be programmed to automatically make adjustments to an implant based on programmed data and/or data obtained from the implant.

A power supply 2003 may be coupled to the processor/controller 2001, memory 2002, and/or operative modules 2004 in order to provide operative energy. The power supply 2003 may take any form described in this disclosure (e.g., a similar device as power supply 1003), may plug into an electrical socket, or use any other power or energy supply known in the art.

The power supply 2003 may also be managed by a power management strategy depending on the power demands. For example, the power management might institute powered, sleep, and idle cycles. In some cases, the power management strategy might take into account the total power and total intended useful life of ERC 2000. In some cases, the power management strategy is implemented by the processor/controller 2001.

Additionally, a Display/DI may be onboard or external to ERC 2000. For example, Display/DI 2008 is shown as onboard ERC 2000. However, Display/DI 2008 may also be external and connect to ERC 2000 (e.g., in communication with processor/controller 2001) through wireless or wired data paths, such as high-definition multimedia interface, display port, Bluetooth (e.g., Bluetooth low energy), Zig-Bee, Wi-Fi, induction wireless data transmission, medical implant communication service (MICS), radio frequencies, near-field communication (NFC), global system for mobile communications (GSM), or any other form of data transmission known in the art. In some embodiments, Display/DI 2008 comprises a touch screen, monitor, television, liquid-crystal display, or any other way of visually showing information. Display/DI 2008 may also include a touch panel, button-selection, keyboard, mouse, voice input, roller ball, gesture interface, or any other way of inputting information known in the art. In some cases, Display/DI 2008 may be coupled to a speaker or sound-producing device that can, for example, play audio data, beep, or sound an alarm.

In some circumstances, it may be desirable for Display/DI 2008 to show measured parameters and/or biological conditions to a care provider. The care provider can then make treatment decisions based on the displayed information. For instance, Display/DI 2008 may show the displacement of sensors attached to the implantable device. If the sensors are attached to two points on a bone, and the sensors move farther apart, this occurrence might suggest that osteogenesis and/or bone lengthening is occurring. The care provider may then increase or decrease the force placed on the bone or the adjustment rate as a result of reviewing this information. In some cases, the care provider may directly control the force outputted by the implant. For example, the care provider may send instructions to ERC 2000, which can be uploaded to implant 1000. Alternatively, in some embodiments, the care provider may send instructions directly to implant 1000.

In other embodiments, the care provider can send limits to ERC 2000, where the amount of control that a patient has in adjusting implant 1000 with ERC 2000 is limited to a range of values. For example, the care provider can put in safety cutoffs and/or override features. In some circumstances the care provider or patient can shut down implant operation entirely using an override control, such as if there is an emergency.

In some cases, ERC 2000 may be additionally coupled to an imager, such as an ultrasound, x-ray, magnetic resonance imaging, or computed tomography. In some cases, it may be desired to couple the external remote controller with a portable imager, such as an ultrasound, in order to image the bone region. This information can be displayed with Display/DI 2008 and/or transmitted to an external device for viewing by a user (e.g., a care provider). The images can provide additional information concerning bone healing, therapeutic progression, and/or other clinically relevant data. The additional information can further inform adjustment of a bone reshaping implant.

An illustrative interaction between implant 1000 and ERC 2000 is as follows. Implant 1000 detects a measurable parameter indicative of a biological condition (e.g., using sensor 1005). Implant 1000 then transmits data to ERC 2000 (e.g., continuously, periodically, or in response to interrogation). The data may be raw data for ERC 2000 to process, or data already processed by implant 1000. ERC 2000 can then interpret the data in view of stored patient information and/or display the data to a care provider. The ERC 2000 then transmits instructions to the implant 1000, and the implant 1000 acts in response to those instructions. In some cases, the implant 1000 may also transmit post action status information to ERC 2000, such as a treatment history.

For example, for certain patients undergoing a femoral bone lengthening procedure, the optimal rate of distraction may be approximately 1 mm per day. However, the rate of osteogenesis may vary from patient to patient, as well as the discomfort level associated with different rates of distraction. Feedback recorded by the implant indicative of the rate of osteogenesis may be utilized to optimize the distraction rate for given circumstance. Strain gauge data or other data from on onboard sensor may be utilized to monitor the progress of osteogenesis. That data may be retrieved from the implant by the ERC, which internally, or in combination with clinical personnel, can determine that a particular patient can or should have a reduction in distraction rate to no more than about 0.5 mm per day or no more than about 0.75 mm per day. Alternatively, the implant and control systems disclosed herein, either internally or in combination with clinical staff, may determine in a given instance that the patient might benefit from or is willing to increase the distraction rate to no more than about 1.5 mm or no more than about 2 mm per day.

In addition, the ERC may optionally be provided with a fine tuning adjustment to be made by the patient. This would enable the patient to deviate from the programmed distraction rate by an increase or decrease from the preset rate in an amount of no more than about 5%, in some implementations no more than about 10%, and in other implementations no more than about 25%. Attempts to make adjustments outside of the predetermined bracket limits would have no effect. In this manner, the patient would be given sufficient control to enable fine tuning of the distraction rate to take into account discomfort levels or other desires of the patient.

Figure 3:
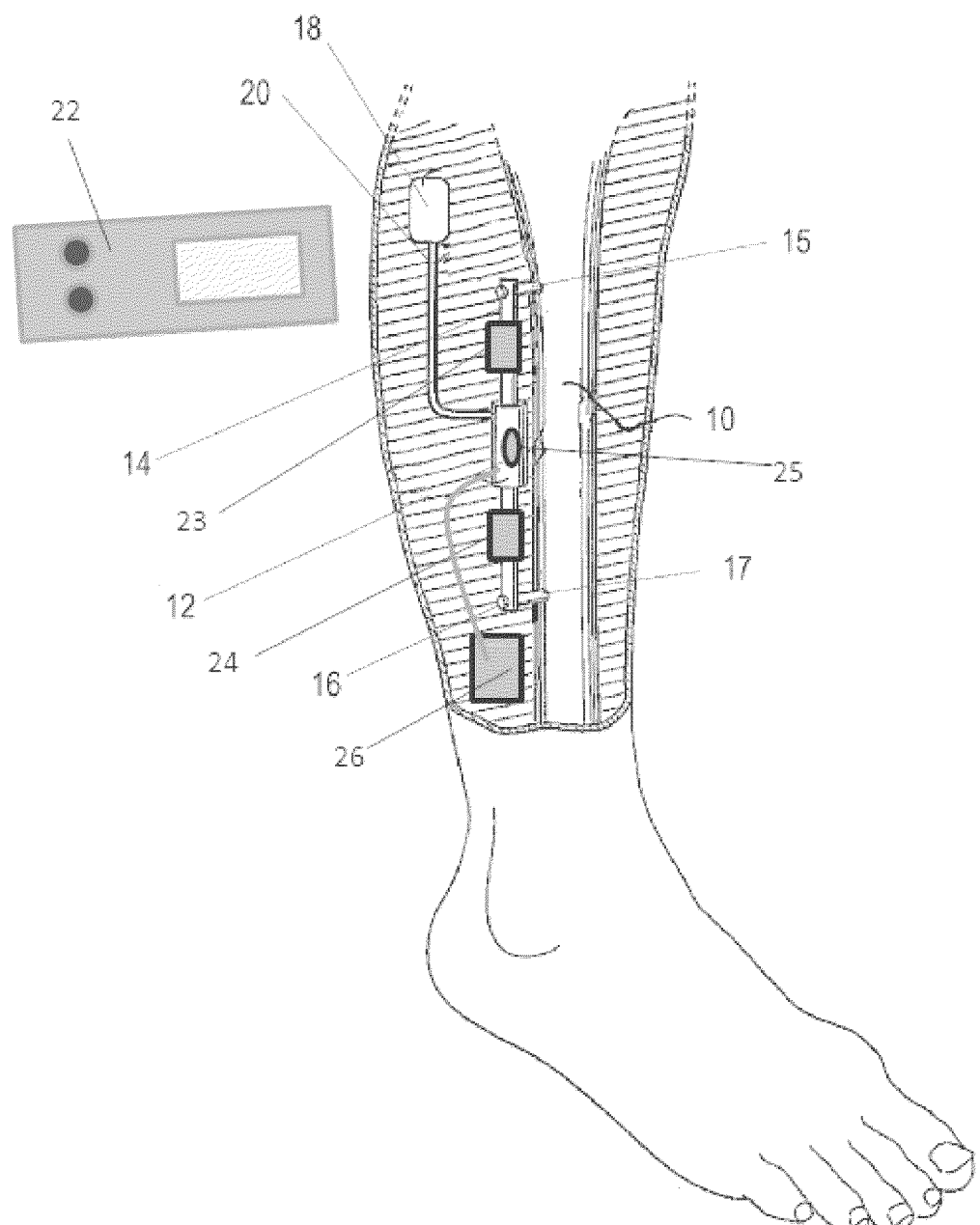
FIG. 3 shows one embodiment illustrating how an implant may attach to a bone and communicate with an external remote controller.

FIG. 3 illustrates one embodiment. The unmodified tibia 10 has a bone reshaping implant 12 attached thereto. The bone reshaping implant 12 may be configured for axial expansion or compression, and/or torsion or other movement necessary to achieve the desired clinical result.

Bone reshaping implant 12 is provided with at least a first attachment point 14 and a second attachment point 16 for attachment to the bone 10. In the illustrated embodiment, first and second attachment points 14 and 16 may be apertures for receiving a first bone screw 15 and a second bone screw 17. Attachment of the implant 12 to the bone 10 may be accomplished in any of a variety of ways, such as by utilizing one or two or more bone screws at each of the first and second attachment points. Alternatively, the first and second attachment points may be connected to a plate, adhesively secured to the bone, secured to a collar or ring which surrounds at least a portion or potentially encircles the bone, or other attachment structure having sufficient structural integrity to achieve the desired clinical result.

The portion of bone located between the first bone screw 15 and second bone screw 17 is the treatment zone, over which forces generated by the bone reshaping implant 12 will be distributed. Although not illustrated, the bone 10 in between the first bone screw 15 and second bone screw 17 will normally contain one or more bone deformities, the correction of which is desired. Also not pictured, the bone 10 in between the first bone screw 15 and second bone screw 17 may contain a bone injury, such as a fracture.

One or more sensors 23 and 24 may be provided. The one or more sensors may be fixed to a location on the implant body 12. The sensors may also be desirably located on the connection points 15 and 17, or to locations in contact with the bone. The sensors 23 and 24 are configured to measure a parameter indicative of a biological condition (e.g., osteogenesis or any of the biological conditions described in this disclosure). They may also be of any type (or combination of any type) described in this disclosure or known in the art. For example, in the particular configuration illustrated, the two sensors 23 and 24 may sense stress (strain gauge) or a distance between each other using, for example, light such as infrared (IR) light, lasers, electric current, inductance, film resistors, acoustics, or any other way of measuring distance between objects known in the art. This distance measurement may be correlated to osteogenesis. For example, if the sensors are moving farther away from each other, successful osteogenesis may be occurring, thereby lengthening the distance between the sensors.

Processor 25 may interpret the outputs of the sensors to calculate a measured parameter. For example, in measuring a strain on the bones, sensors 23 and 24 may output an electric current that is correlated with strain. Processor 25 may then calculate the strain based on those electrical outputs. Additionally, processor 25 may also compile data obtained by sensors (e.g., strain over time and/or the different parameters measured by sensors) for a biological conclusion. For example, by factoring pH, temperature, strain, and displacement, the processor 25 may determine whether osteogenesis is occurring and also an indicium of the rate and circumferential regularity or irregularity of osteogenesis. Processor 25 may additionally calculate an amount of force, an amount of increased force, or an amount of decreased force that could be applied to the bone for effective therapeutic treatment or increasing efficacy of treatment.

In some embodiments, the processor 25 may control a modification of treatment. For example, the processor 25 may drive an actuator coupled to the implant body 12, where the actuator may change the amount or angle of force applied to the bone. For example, implant body 12 may contain motors, magnetic coils, and/or elastic members that contract or expand the implant body 12. The contraction may put more compressive force on at least one side of the bone, whereas the expansion may put more distractive force on at least one side of the bone. In either case, the implant body 12, because of its location on one side of the bone, may also put an angular force on the bone.

One or more transceivers 18 may also be provided. The transceiver 18 may be in communication with the bone reshaping implant 12 or the one or more sensors 23 and 24 by a cable 20, or in other embodiments, wirelessly. Transceiver 18 may alternatively be within, or carried by, the implant. Cable 20 may include electrical, optical, fluid, or other conduit, depending upon the functionality of the implant. The transceiver 18 may be configured for transmitting and receiving information. For example, the transceiver 18 may be configured to communicate to an external device using any of the modalities previously mentioned, such as induction wireless data transmission or any other form of wireless data transmission. In some embodiments, the transceiver 18 is configured to transmit data to ERC 22. The data may be data generated by sensors 23 and 24, data outputted by the processor 25, status information, a biological condition, a request for information from an external device, or any other relevant information described in this disclosure.

In some embodiments, transceiver 18 may be configured to transmit data continuously. Such continuous transmission might be desirable in order to allow an external remote control to monitor the patient's conditions and undertake reactive measures when necessary. However, in some circumstances, continuous transmission may require more power, and could lead to low battery life for the implantable device. In other embodiments, transducer 18 may be configured to transmit data periodically, such as every minute, every hour, every day, every week, every month, every year, and/or any period of time, including any time between any two of the aforementioned periods of time. In other embodiments, transceiver 18 may be configured to transmit data in response to an interrogation signal by an ERC 22 or some other external device. In still other embodiments, transceiver 18 may be configured to transmit data in response to an event, for example a sudden change in a measured parameter, reaching a preset trigger threshold in a measured parameter, a detected biological condition, or a change in implant status (e.g, damage to the implant or the implant is out of batteries).

Transceiver 18 may also be configured to receive data transmitted from an ERC 22. This data may contain instructions, such as directions for the processor to drive the actuator. It may also provide a status or request for the transceiver to send data. It may also provide firmware updates and/or updates to algorithms, protocols, or therapies.

In some embodiments, a power supply 26 may also be provided. The power supply 26 may be a battery or any power supply discussed in this disclosure. Power supply may be carried within or on the implant 12, or near the implant as illustrated.

In some embodiments, a memory may be coupled to processor 25 in order to store, for example, processor data, firmware, instructions, power management data, and information to be outputted by the transceiver on interrogation.

ERC 22 may be an ERC with the same functionalities as ERC 2000. In particular, ERC 22 may be in communication with transceiver 18 to receive data from the implant and send responsive instructions to the implant. In some cases, the implant acts in response to ERC 22's instructions. For example, ERC 22's instructions may cause an actuator coupled to implant body 12 to actuate.

Figure 4:
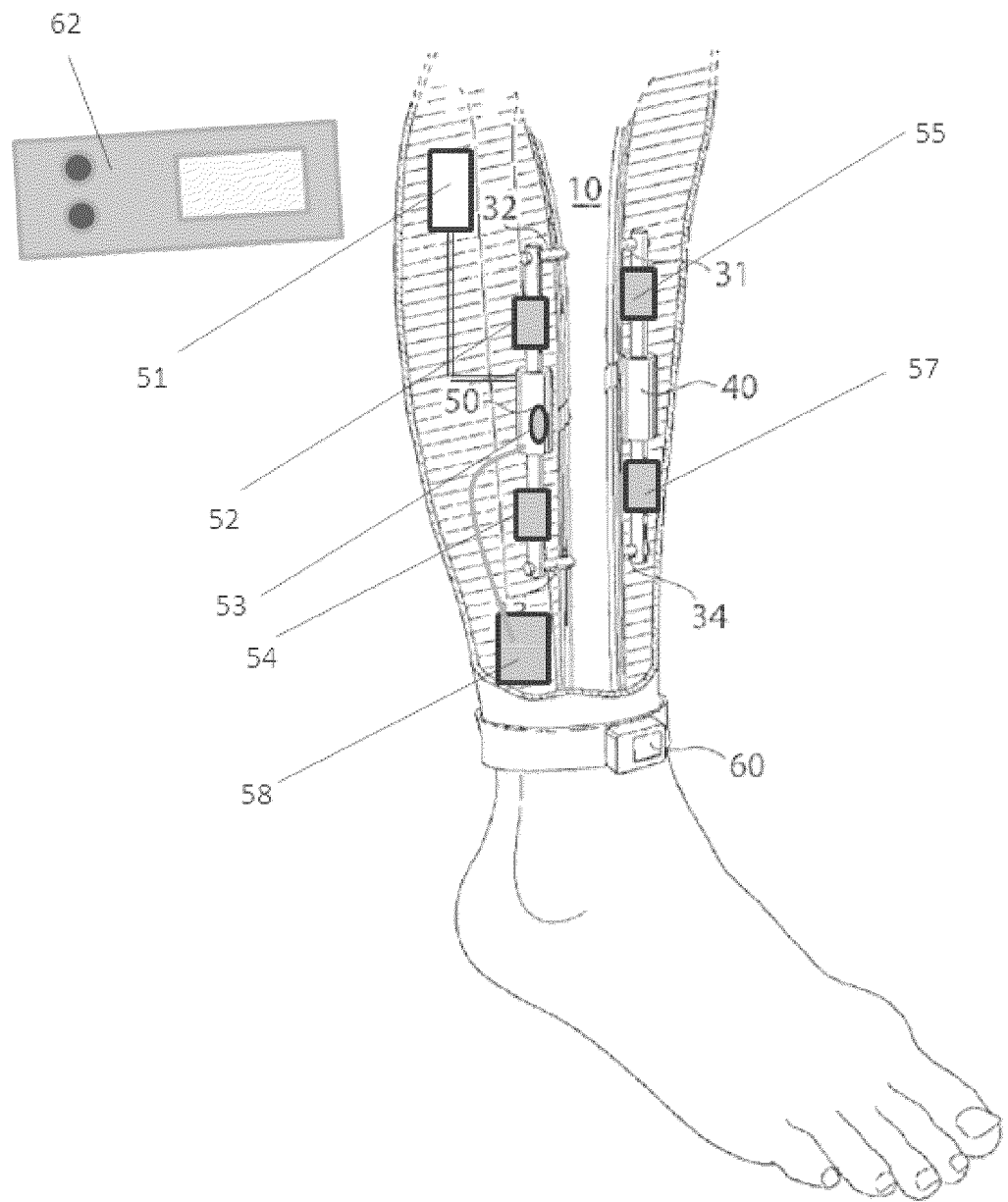
FIG. 4 shows another embodiment illustrating how an implant may be attached to two sides of a bone and may also be in communication with an external remote controller.

FIG. 4 illustrates another embodiment. This embodiment has two bone reshaping implant bodies 40 and 50. In some embodiments, each of implant body 40 and 50 may be coupled to its own sensors. For example, implant body 40 has sensors 55 and 57, and implant body 50 has sensors 52 and 54. There may be one or more internal or external power supply 58 as desirable to power the implants. There may also be one or more internal or external transceivers 51 as desirable to transmit and receive information for the implant bodies 40 and 50. There may also be one or more processors 53 as desirable to process data.

Having two (or more) implants, such as implants 40 and 50, on a bone may be desirable in certain situations in order to better support the bone structure. These implants may be operated jointly or independently, depending on therapeutic applications. For example, two implants putting the same pressure in the same direction on the bone simultaneously from two sides may prevent or tend to correct curvature and/or other deformities to bones during osteogenesis. On the other hand, to improve bone curvature, further angular force may be placed on a bone by compressing one implant and distracting the other, and/or applying different forces to the different implants. In still another application, osteogenesis may occur, in some circumstances, at different rates across a bone. Using multiple implants can compensate for these bone growth differences by applying compensatory compression or distraction therapies.

It should be appreciated that there may be many configurations in which one or more implants may be fixed to bones. For example, there are configurations in the art using four or more implant bodies attached to a femur or spine at various points. Embodiments of the present disclosure are not limited to any particular formation or way of attaching implants to bones.

Figure 5:
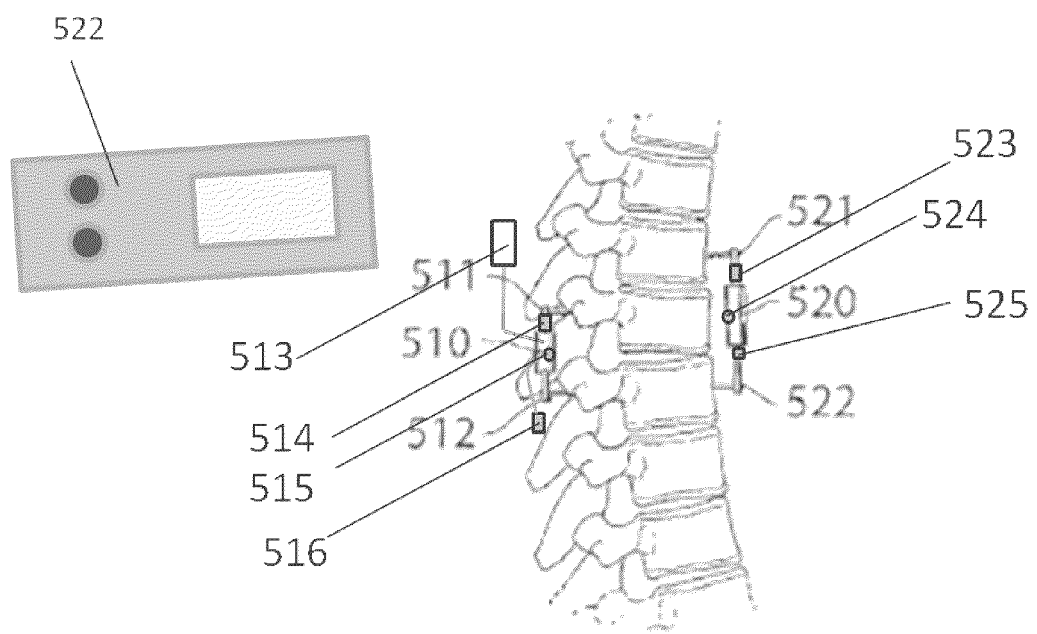
FIG. 5 shows another embodiment illustrating how an implant may be attached to vertebrae and may also be in communication with an external remote controller.

FIG. 5 illustrates that similar implantable devices may be placed in other parts of the body. For example, one or more implantable devices 510 and 520 may be implanted along the spine in order to adjust the curvature of the spine. For illustrative purposes, implant 510 is shown attached to two adjoining vertebrae by two anchoring devices 511 and 512, whereas another device 520 is shown typically in a separate procedure (both illustrated on the same bone for convenience) attached to non-adjoining vertebrae by two anchoring devices 521 and 522. This embodiment can be used to adjust the curvature of the spine, such as to relieve a herniated lumbar disc or the like.

Figure 6:
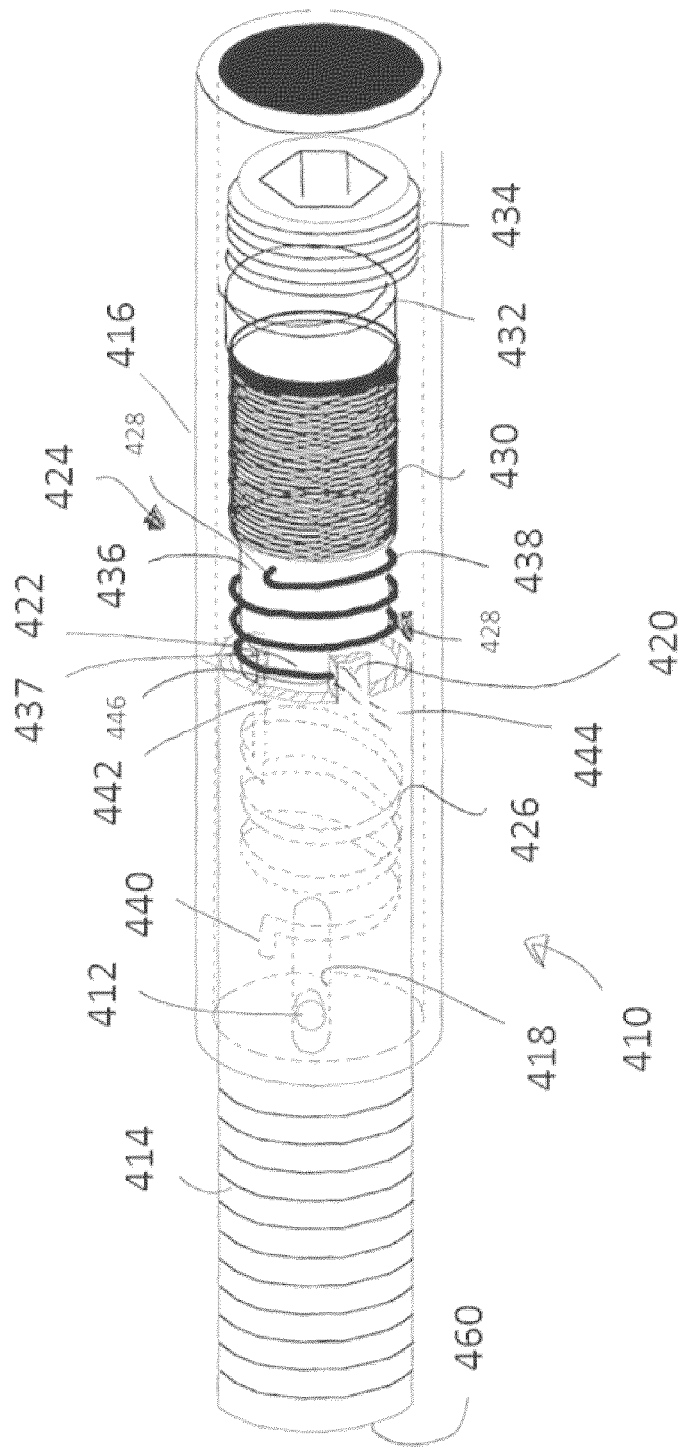
FIG. 6 is an example of an implantable device that can be adjusted by external stimulus.
Figure 7:
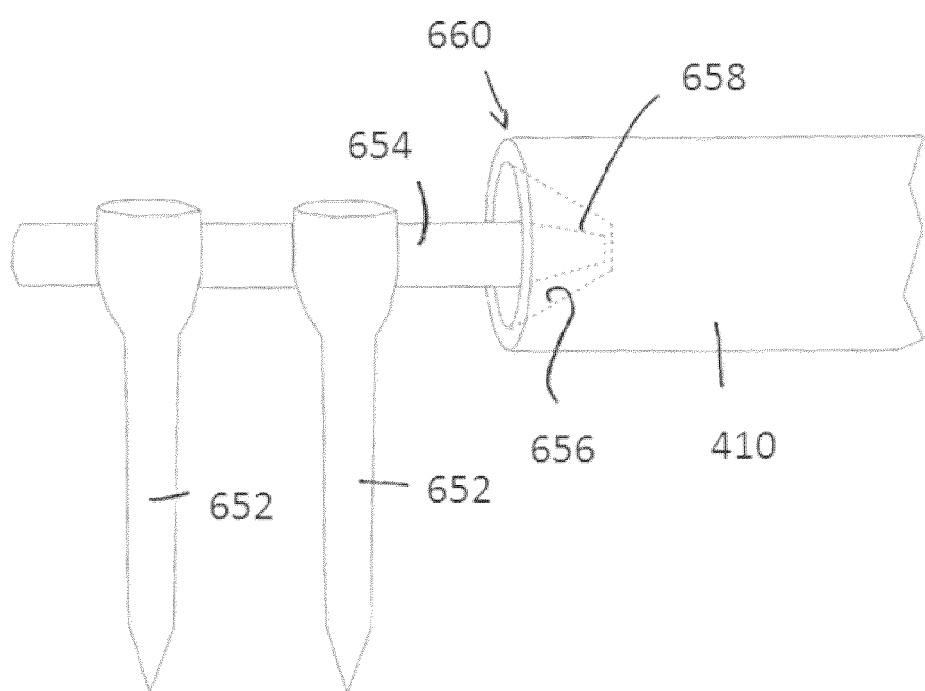
FIG. 7 is an example of how an implantable device may be attached to a bone using screws.

In some embodiments, the implant is configured to be adjusted externally. For example, FIG. 6 shows an expanding or telescopic rod 410. The opposing ends of rod 410 are fixed to selected positions on the bone using conventional surgical screws. For example, rod 410 may be fixed to a bone using screws 542 as depicted in FIG. 7 or FIG. 3. Additionally, or alternatively, rod 410 may be used as an intermedullary implant, or as part of or in conjunction with implants 12, 40, 50, 510, and/or 520. In this way, it should be appreciated that the externally controlled adjustments to rod 410 can be made based on measured parameters indicating biological conditions. For example, the sensors of implants 12, 40, 50, 510, and/or 520 can transmit relevant data or information, as described in this disclosure, to an ERC. The ERC, or a care provider, can use the information to determine if the ERC should adjust the implant.

The rod 410 may produce a controlled force, slowly over time, under precise external control, and be isolated or implanted completely under the skin and protected by the natural barrier, which the skin provides. Rod 410 may also be small, powerful, simple enough to be readily manufactured, immune to accidental activation, and biologically inert.

The pick-up coil 430 receives energy from an external hand-held source of energy, such as a low frequency generator of electromagnetic radiation, which is brought into proximity with coil 430. Some examples of such a hand-held source of energy are ERC 22, 62, and/or 522. Rod 410 is implanted beneath the skin barrier, while the source of energy is exterior to the body. The external inductive power source may be driven at conventional line frequency. In the event that the coil 430 is to be able to efficiently drive the muscle wire 438, then either a storage capacitor with a control diode can be added in circuit with coil 430, or with more complexity, a battery with a diode voltage multiplier, and control diode could be used. Any means of impedance matching between coil 430 and wire 438 on one hand and between coil 430 and the inductive power source on the other may be employed. The use of external power sources and inductively powered implanted coils is well known to the art and are routinely used, for example, in charging implanted pacemaker devices.

In some alternatives, energy can be fed into the pick-up coil until enough is stored in the capacitor to drive the motor 428. Upon the firing of the motor 428, the hand-held device could sense the discharge, and shut-off for the prescribed lock-out period. In other alternatives, an on-board battery or power supply assists in charging the capacitor, and thus requires significantly more control electronics. For example, such an onboard battery or power supply may be power supply 26, 58, and/or 516.

In certain embodiments and alternatives, an internal processor, such as processors 25, 53, and/or 515 may additionally control the power supply and/or motor 428, such as by enabling or disabling the extension/contraction of rod 410, or by placing limits on such extension/contraction. The processor may also process further instructions, data, statuses, etc. from an ERC.

Figure 8:
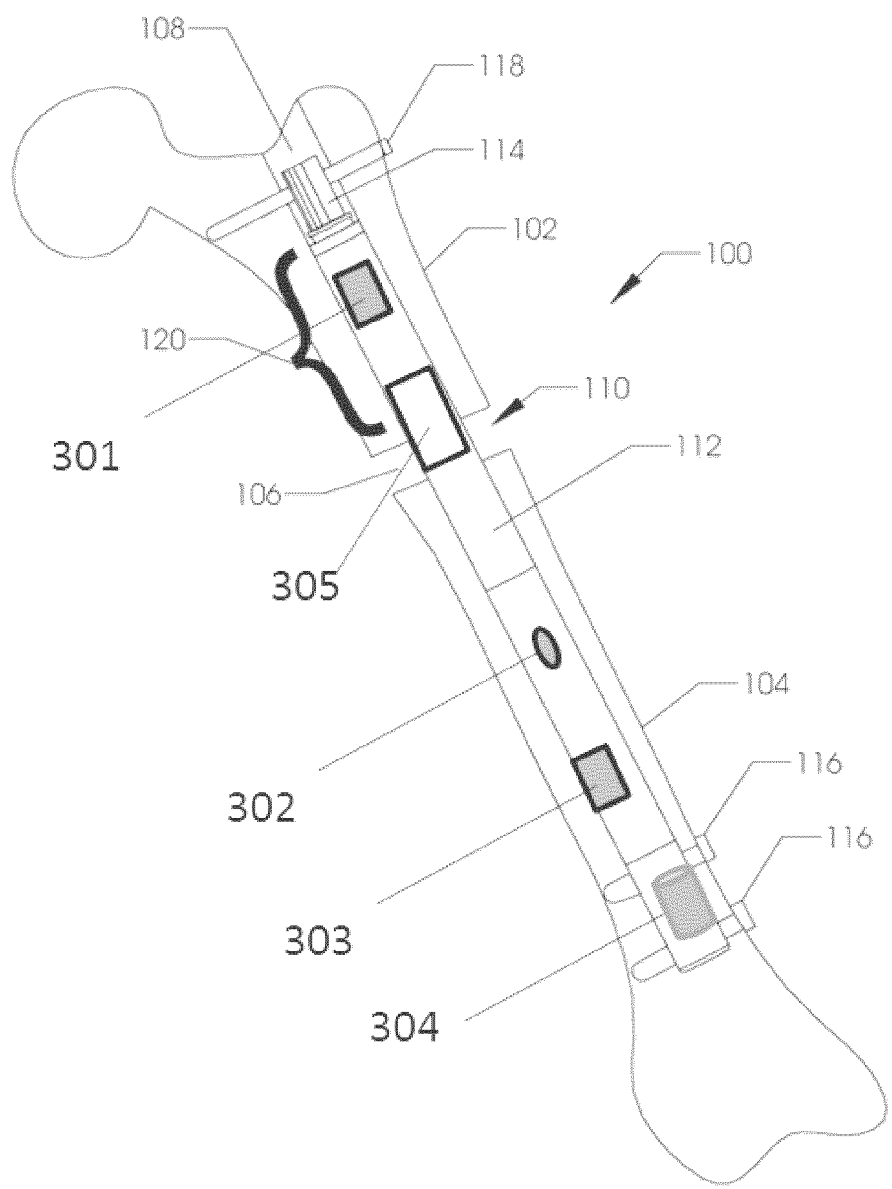
FIG. 8 illustrates an example embodiment having an implantable intramedullary device.

In some cases, an implant may be placed inside a bone, such as inside the medullary canal. FIG. 8 shows such an implant 110, placed inside a bone. The implant has at least one, and in the illustrated implementation two sensors 301 and 303 such as strain gauges or other disclosed elsewhere herein, coupled to the implant body. It also has processor 302, power supply 304, and transceiver 305.

FIG. 9 further details one particular implant 110 and how it actuates. The implant 110 has one or more distraction shaft screw holes 122 in the distraction shaft 114 through which the screws may be placed. Likewise, the housing 112 is attached to an end cap 130 which has one or more housing screw holes 124 through which the screws may be placed. FIG. 10a shows that the housing 112 of the intramedullary lengthening device 110 includes a magnet housing 128 and splined housing 126. The housings 126, 128 may be attached to each other by means of welding, adhesive bonding, or other joining techniques. The magnet housing 128 is sealably closed at one end (the end opposite the interface with the splined housing 126) by the attachment of the end cap 130. The end cap 130 may be attached to the magnet housing 128 by means of welding, adhesive bonding, or other joining techniques. In use, the distraction shaft 114 is driven from the housing 112 by means of a lead screw 136 which turns inside a nut 140 that is secured to an inner surface adjacent to a cavity 137 of the distraction shaft 114. The lead screw 136 is mechanically coupled, in an indirect manner, to cylindrical permanent magnet 134 contained within the magnet housing 128. Rotation of the cylindrical permanent magnet 134, which is magnetically driven by an external adjustment device 180 (FIG. 11), effectuates rotation of the lead screw 136.

Cylindrical magnet 134 is fixedly contained within a magnet casing 158 using, for example, an adhesive such as an epoxy. The magnet casing 158 rotates relative to the magnet housing 128. The cylindrical magnet 134 may be a rare earth magnet such as Nd—Fe—B and may be coated with Parylene or other protective coatings in addition to being protected within the magnet casing 158, for example hermetically potted with epoxy. The magnet casing 158 contains an axle 160 on one end which attaches to the interior of a radial bearing 132. The outer diameter of the radial bearing 132 is secured to the interior of a radial bearing 132. The outer diameter of the radial bearing 132 is secured to the interior of the end cap 130. This arrangement allows the cylindrical magnet 134 to rotate with minimal torsional resistance. At its other, opposing end, the magnet housing 158 includes an axle 161, which is attached to a first planetary gear set 154. Shown in FIG. 10b, the axle 161 includes the sun gear of the first planetary gear set 154, the sun gear turning the planetary gears of the first planetary gear set 154. The first planetary gear set 154 serves to reduce the rotational speed and increase the resultant torque delivery from the cylindrical magnet 134 to the lead screw 136. A second planetary gear set 156 is shown between the first planetary gear set 154 and the lead screw 136, for further speed reduction and torque augmentation. The number of planetary gear sets and/or the number of teeth in the gears may be adjusted, in order to achieve the desired speed and torque delivery. For example, a lead screw with eighty (80) threads per inch attached to two planetary gear sets of 4:1 gear ratio each inside a 9 mm device with magnet location in the distal femur can achieve at least 100 lb. of distraction force at a greater than average distance or gap from the external device.

Figure 12:
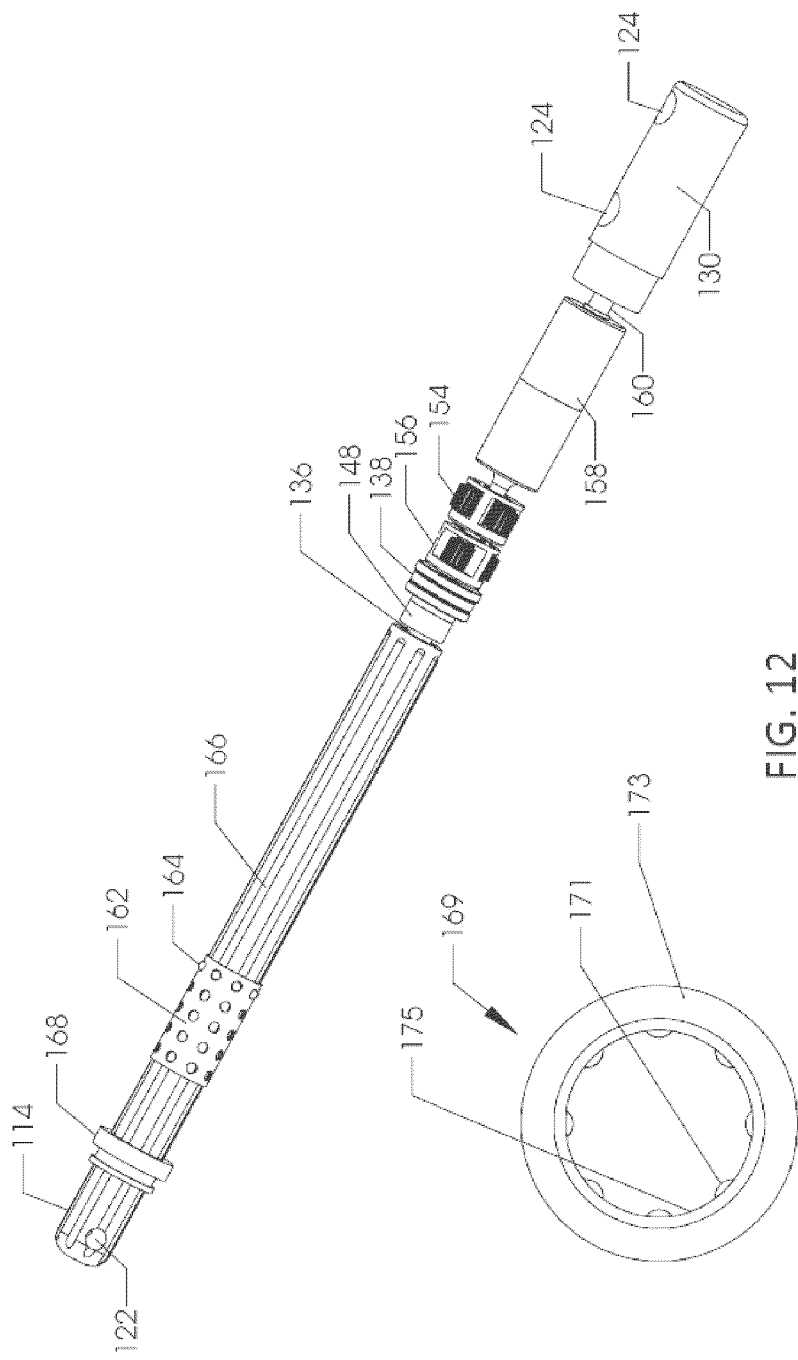
FIG. 12 illustrates a perspective view of some of the internal components of the device of FIG. 9.

In FIG. 12, the housing components have been removed to reveal various internal features, including a collar that allows sliding of the distraction shaft 114 within the housing 112, and which also keeps the distraction shaft 114 from being able to rotate within the housing 112. This allows full stability of the bone 100.

Figure 11:
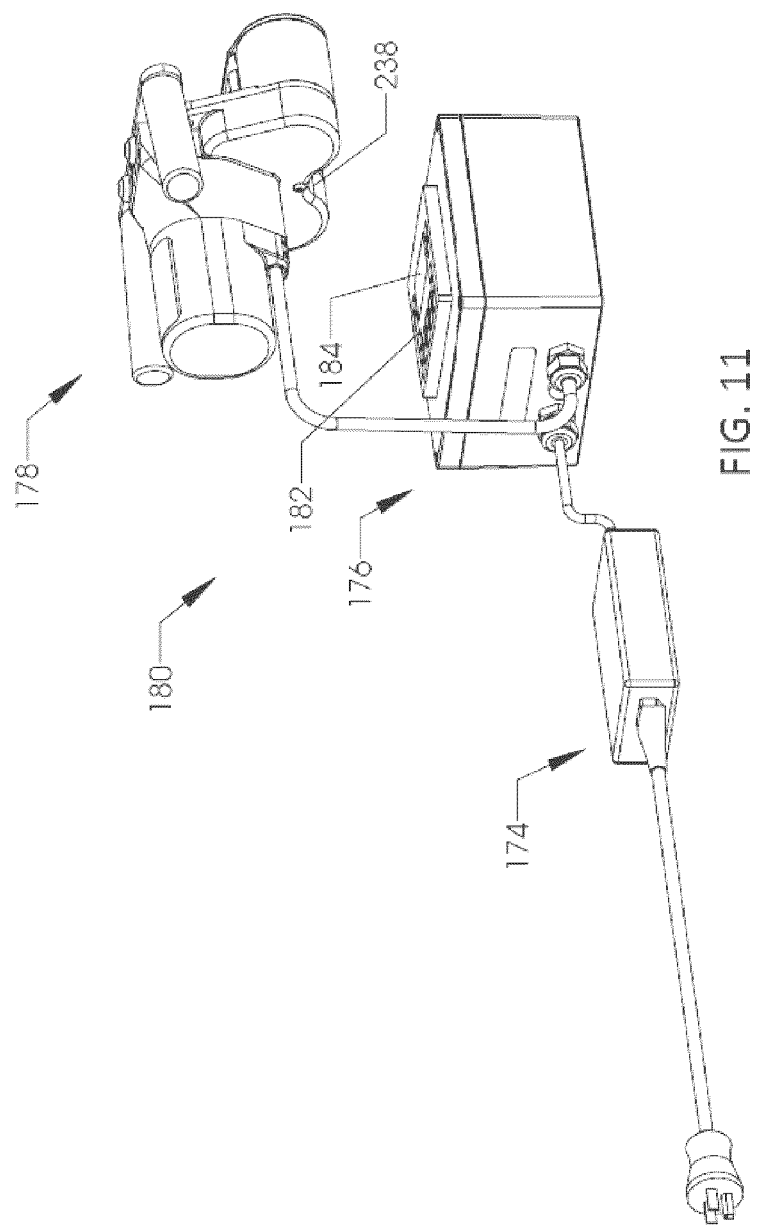
FIG. 11 illustrates an example external remote controller for wirelessly controlling and communicating with the implantable device of FIG. 8.

FIG. 11 illustrates an example of an ERC 180 which is used to non-invasively control the bone reshaping implant 110 by means of a magnetic coupling which transmits torque. ERC 180 comprises a magnetic handpiece 178 (e.g., a mover), a control box 176 (containing a processor), which may be integrated with the handpiece, and a power supply 174 such as a battery or external plug for connection to a standard power outlet. The control box 176 includes a control panel 182 having one or more controls (buttons, switches or tactile, motion, audio or light sensors) and a display 184. The display 184 may be visual auditory, tactile, the like, or some combination of the aforementioned features, or any other display/DI described in this disclosure. The control box 176 may further contain a transceiver for communication with transceiver 305 of the implant and/or other external devices. With implant 110, the transceiver may obtain or send information including raw data (e.g., changes in electrical current), measured parameters (e.g., temperature, displacement, or strain), processed information (e.g., a status, or biological condition), instructions, interrogatory signals, or any other data, information, or signal relevant to the implant or external device. With another external device, ERC 180 may send and receive, for example, diagnostic, status, treatment information, and/or any data obtained from the implant to a care provider so that the care provider can evaluate the performance of an implantable device, such as implant 110, and provide services to the patient.

The ERC 180 may also be programmed and/or implement protocols based on data obtained from the implant. For example, ERC 180 (or a care provider) may determine that the rate of compression or distraction should be slowed or accelerated, and adjust the implant accordingly. Alternatively, the ERC may display an appropriate adjustment for the patient to input or cause the ERC to transmit to the implant. Additionally, in some circumstances, ERC 180 may limit a user's ability to make adjustments to therapy depending on therapeutic limits.

A person/one having ordinary skill in the art would further appreciate that any of the various illustrative logical blocks, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the aspects disclosed herein and in connection with the figures may be implemented within or performed by an integrated circuit (IC), an access terminal, or an access point. The IC may include a general purpose processor, a digital signal processor (DSP), an application specific integrated circuit (ASIC), a field programmable gate array (FPGA) or other programmable logic device, discrete gate or transistor logic, discrete hardware components, electrical components, optical components, mechanical components, or any combination thereof designed to perform the functions described herein, and may execute codes or instructions that reside within the IC, outside of the IC, or both. The logical blocks, modules, and circuits may include antennas and/or transceivers to communicate with various components within the network or within the device. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The functionality of the modules may be implemented in some other manner as taught herein. The functionality described herein (e.g., with regard to one or more of the accompanying figures) may correspond in some aspects to similarly designate "means for" functionality in the appended claims.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, optical disk storage, magnetic disk storage or other magnetic storage devices, or any other medium that may be used to store desired program code in the form of instructions or data structures and that may be accessed by a computer. Also, any connection can be properly termed a computer-readable medium. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

It is understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. An implantable device comprising:
   an implant body;
   an actuator coupled to the implant body;
   a first sensor directly connected to the implant body and configured to detect a measurable parameter indicative of a biological condition including at least one of the following: osteogenesis, ossification, osteoconduction, osteoinduction, osteopromotion, additional bone fractures, brittle bones, or improper bone healing;
a transceiver configured to transmit data associated with the measurable parameter to an external remote control and receive instructions from the external remote control;
a memory disposed within the implant body; and
a controller coupled to the memory and configured to adaptively adjust the actuator in response to the measurable parameter detected by the sensor, information stored in the memory, and the instructions received from the external remote control, wherein the actuator adjusts the implant body,
a second sensor directly connected to the implant body and configured to detect a measurable parameter indicative of a biological condition;
wherein the implantable device is configured for insertion along a spine of a patient to make an adjustment to a curvature of the spine, and
wherein the first sensor and the second sensor include two distinct sensors each fixed to a distinct location on the implant body, wherein the actuator is located between the two distinct sensors along the implant body.

2. The implantable device of claim 1, wherein the implant body further comprises a first anchoring device configured to couple the implant body to a first vertebra, and a second anchoring device configured to couple the implant body to a second vertebra.

3. The implantable device of claim 2, wherein the first vertebra and the second vertebra are adjacent vertebrae.

4. The implantable device of claim 2, wherein the first vertebra and the second vertebra are non-adjacent vertebrae.

5. The implantable device of claim 2, wherein the adjustment comprises applying compression between the first anchoring device and the second anchoring device.

6. The implantable device of claim 2, wherein the adjustment comprises applying force to lengthen the distance between the first anchoring device and the second anchoring device.

7. The implantable device of claim 2, wherein the measurable parameter is a distance between the first anchoring device and the second anchoring device.

8. The implantable device of claim 2, wherein the measurable parameter is a motion between the first anchoring device and the second anchoring device.

9. The implantable device of claim 1, wherein the biological condition is a herniated lumbar disc.

10. The implantable device of claim 1, wherein the information stored in the memory comprises at least one of data associated with the measurable parameter, data associated with the instructions received from the external remote control, and status information.

11. The implantable device of claim 1, wherein the measurable parameter is at least one of blood flow, temperature, strain, pH, stress, bone composition, bone mass, bone density, bone thickness, bone perfusion, bone strength, bone oxygenation, electrical conductivity, and a presence of active media.

12. The implantable device of claim 1, further comprising a power supply.

13. The implantable device of claim 12, wherein the power supply is configured to be charged by the external remote control.

14. The implantable device of claim 1, further comprising an energy receiving element configured to receive energy from an external source.

15. The implantable device of claim 1, wherein the sensor is fixed to a location on the implant body.

16. The implantable device of claim 1, wherein the sensor is aligned with an axis of the implant body.

17. The implantable device of claim 1, wherein the sensor is directly adjacent to the actuator.

18. An implantable device comprising:
an implant body;
an actuator coupled to the implant body;
a plurality of sensors each directly connected to the implant body and configured to detect a measurable parameter indicative of a biological condition;
a transceiver configured to transmit data associated with the measurable parameter to an external remote control and receive instructions from the external remote control;
a memory disposed within the implant body; and
a controller coupled to the memory and configured to adaptively adjust the actuator in response to the measurable parameter detected by the plurality of sensors, information stored in the memory, and the instructions received from the external remote control, wherein the actuator adjusts the implant body,
wherein the implantable device is configured for insertion along a spine of a patient to make an adjustment to a curvature of the spine, and
wherein the plurality of sensors includes two distinct sensors each fixed to a distinct location on the implant body, wherein the actuator is located between the two distinct sensors along the implant body.

19. The implantable device of claim 18, wherein each of the plurality of sensors is aligned with an axis of the implant body.

* * * * *